(12) United States Patent
Raymo et al.

(10) Patent No.: US 8,198,099 B2
(45) Date of Patent: Jun. 12, 2012

(54) MECHANISM TO SIGNAL RECEPTOR-LIGAND INTERACTIONS WITH LUMINESCENT QUANTUM DOTS

(75) Inventors: Francisco M. Raymo, Coral Gables, FL (US); Massimilliano Tomasulo, Miami, FL (US); Ibrahim Yildiz, Miami, FL (US)

(73) Assignee: The University of Miami, Miami, FL (US)

( * ) Notice: Subject to any disclaimer, the term of this patent is extended or adjusted under 35 U.S.C. 154(b) by 470 days.

(21) Appl. No.: 12/307,878

(22) PCT Filed: Jul. 9, 2007

(86) PCT No.: PCT/US2007/015636
§ 371 (c)(1),
(2), (4) Date: Dec. 30, 2009

(87) PCT Pub. No.: WO2008/005561
PCT Pub. Date: Jan. 10, 2008

(65) Prior Publication Data
US 2010/0112560 A1    May 6, 2010

Related U.S. Application Data

(60) Provisional application No. 60/818,964, filed on Jul. 7, 2006.

(51) Int. Cl.
*G01N 33/551* (2006.01)

(52) U.S. Cl. ......... 436/524; 435/6.1; 436/172; 436/525; 436/805

(58) Field of Classification Search ........................ None
See application file for complete search history.

(56) References Cited

U.S. PATENT DOCUMENTS

2003/0003492 A1    1/2003    Miller et al.
2005/0064604 A1    3/2005    Bohmann et al.

OTHER PUBLICATIONS

Raymo et al. "Luminescent chemosensors based on semiconductor quantum dots" Phys. Chem. Chem. Phys. 9:2036-2043 (2007).
Tomasulo et al. "Luminescence modulation with semiconductor quantum dots and photochromic ligands" Aust. J. Chem. 59:175-178 (2006).
Tomasulo et al. "pH-sensitive quantum dots" J. Phys. Chem. B. 110:3853-3855 (2006).
Tomasulo et al. "pH-sensitive ligand for luminescent quantum dots" Langmuir 22:10284-10290 (2006).
Tomasulo et al. "Nanoparticle-induced transition from positive to negative photochromism" Inorg. Chim. Acta 360:938-944 (2007).
Yildiz et al. "Photocromic nanocomposites of bipyridinium dications and semiconductor quantum dots" J. Mater. Chem. 16:1118-1120 (2006).
Int'l Preliminary Report on Patentability for PCT/US2007/015636, mailed Jan. 22, 2009.
Int'l Search Report for PCT/US2007/015636, three pages, mailed Aug. 7, 2008.
Written Opinion for PCT/US2007/015636, three pages, mailed Aug. 7, 2008.

*Primary Examiner* — Chris L Chin
(74) *Attorney, Agent, or Firm* — Nixon & Vanderhye P.C.

(57) ABSTRACT

Semiconductor quantum dots are becoming valuable analytical tools for use in biomedical applications. Indeed, their unique properties offer the opportunity to design luminescent probes for imaging and sensing with unprecedented performance. In this context, we have identified operating principles to transduce supramolecular association of complementary receptor-ligand binding pairs into enhancement or suppression in the luminescence of sensitive quantum dots. Thus, complementary receptor-ligand binding pairs can be identified with luminescence measurements relying on our design logic. In fact, we have demonstrated with a representative example that our protocol can be adapted to signal receptor-ligand binding.

19 Claims, 6 Drawing Sheets

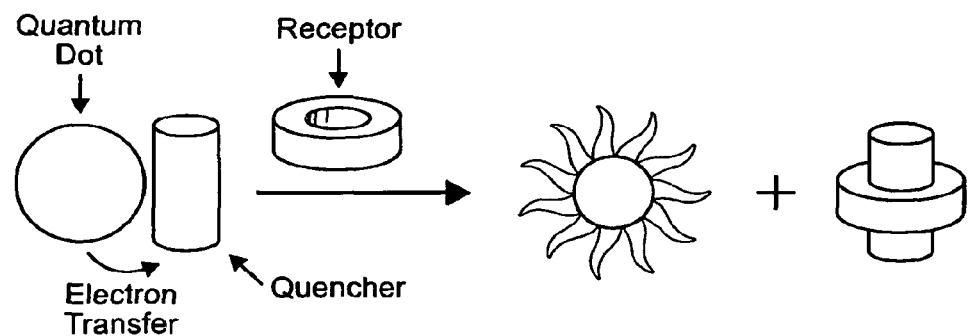
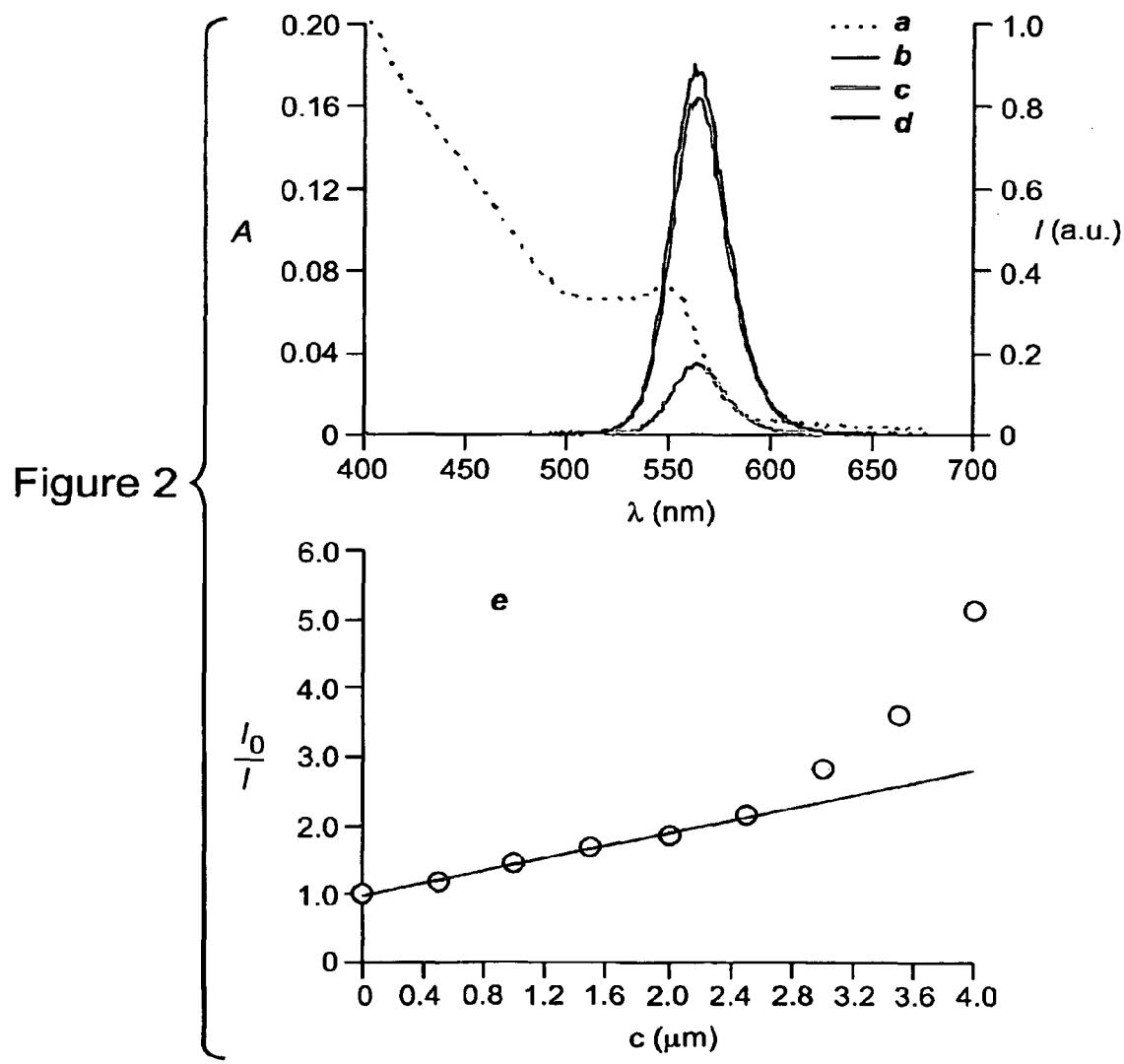
Figure 1
Figure 2

MECHANISM TO SIGNAL RECEPTOR-LIGAND INTERACTIONS WITH LUMINESCENT QUANTUM DOTS

CROSS REFERENCE TO RELATED APPLICATIONS

This application claims priority benefit of provisional U.S. Appliction No. 60/818,964, filed Jul. 7, 2006.

This is the U.S. national-phase application under 35 U.S.C. 371 of International Application No. PCT/US2007/015636, filed 9 Jul. 2007, which designated the U.S. and claims benefit to Provisional Application No. 60/818,964, filed 7 Jul. 2006; the entire contents of each of which are hereby incorporated by reference.

FEDERALLY-SPONSORED RESEARCH OR DEVELOPMENT

The U.S. Government has certain rights in this invention as provided for by the terms of CHE-O237578 awarded by the National Science Foundation.

BACKGROUND OF THE INVENTION

This invention relates to using a change in quantum dot luminescence as a detectable signal in receptor-ligand binding assays. It is a general method for detecting an analyte that is receptor, cognate ligand, or competitors thereof.

Semiconductor quantum dots are inorganic nanoparticles with remarkable photophysical properties.[1-5] In particular, their one- and two-photon absorption cross sections, luminescence lifetimes, and photobleaching resistances are significantly greater than those of conventional organic fluorophores. Furthermore, their broad absorption bands extend continuously from the ultra-violet to the visible region of the electromagnetic spectrum and, therefore, offer a vast selection of possible excitation wavelengths. Instead, their narrow emission bands can precisely be positioned within the visible and near-infrared regions with fine adjustments of their physical dimensions. In fact, pools of quantum dots with different diameters can be designed to emit in parallel at different wavelengths after excitation at a single wavelength, offering the opportunity to implement unprecedented multichannel assays.

Organic dyes do not offer the unique collection of attractive photophysical properties associated with semiconductor quantum dots. Indeed, it is becoming apparent that these inorganic nanoparticles can complement, if not replace, their organic counterparts in a diversity of biomedical applications.[6-12] Nonetheless, decades of intensive investigations on the structure and properties of organic chromophores have indicated valuable strategies to design sensitive fluorescent probes able to signal the presence of target analytes with changes in emission intensity:[13-16] Their operating principles generally rely on the covalent connection of a fluorescent component to a receptor. The receptor is then engineered to quench the emission of the fluorophore on the basis of either electron or energy transfer. The supramolecular association of the receptor with its cognate ligand (e.g., a target analyte), however, suppresses the quenching mechanism and leads to a significant enhancement in fluoresence intensity. Under these conditions, the presence of the target analyte is therefore transduced into a detectable fluorescence signal. In the past, however, it was not entirely clear if and how these strategies could successfully be extended to quantum dots.

Promising studies demonstrated that semiconductor quantum dots can donate energy to complementary partners.[17] In fact, clever assays for the recognition of various analytes are starting to be designed on the basis of energy transfer processes.[18-30] But the use of reaction mechanisms based on electron transfer in receptor-ligand assays remains to be explored and exploited.[31-32]

Therefore, it is an objective of the invention to provide improved compositions for sensing an analyte through receptor-ligand interaction (i.e., binding) and transducing a detectable signal by a change in quantum dot luminescence. Other advantages and improvements are described below or would be apparent from the disclosure herein.

SUMMARY OF THE INVENTION

An objective of the invention is to provide a luminescent quantum dot having a quencher adsorbed thereon for use in a binding assay. For example, a composition may be comprised of: (i) at least one luminescent nanoparticle having a surface and comprising an essentially spherical, semiconductor nanocrystal; (ii) one or more quencher-ligand molecules which may be noncovalently associated on the surface, thereby modulating (e.g., at least decreasing or increasing) a luminescent signal of the nanoparticle, or may be removed from the surface, thereby modulating (e.g., at least increasing or decreasing, respectively) a luminescent signal of the nanoparticle, wherein the molecule(s) are comprised of quencher and ligand moieties; and (iii) one or more receptors which may bind at least one quencher-ligand molecule, and thereby remove at least one quencher-ligand molecule from the surface after binding. At least one nanoparticle may have a mean diameter from 1 nm to 10 nm. At least one nanocrystal may be comprised of CdSe or CdTe. At least one nanoparticle may be coated. The coating may be comprised of an inorganic semiconductor layer (e.g., comprised of ZnS or ZnSe), an organic layer, a hydrophilic organic layer, or any combination of such layers. At least one quencher may be a bipyridinium cation or tertiary amine. At least one receptor may be a nucleic acid or protein. The analyte may be a ligand or its competitor; the may be a receptor or its competitor. The composition may further comprise a physiologically-acceptable carrier. The composition may be tested for sterility (i.e., composition is aseptic) and/or tested for endotoxin or pyrogen (i.e., composition is nontoxic).

A further objective is to provide a kit, which is comprised of one or more containers in a package, further comprising (a) at least one composition and (b) positive control, negative control, calibration standards of a known amount of analyte, or any combination thereof.

It is another objective to provide use of the composition for detection of at least presence (or absence within detection limits) or quantity of an analyte.

To detect at least the presence (or absence within detection limits) or the quantity of an analyte, a method is provided comprising: (a) contacting the composition with a solution which might contain an analyte, wherein binding of receptor and ligand removes quencher molecule(s) from the luminescent nanoparticle's surface; (b) measuring whether or not there is a detectable change in luminescent signal; and (c) correlating the change in luminescent signal with detection of the analyte. Fluorescence absorption of the nanoparticle may be excited at one or more wavelengths from 300 nm to 700 nm; fluorescent emission of the nanoparticle may be measured at one or more wavelengths from 400 nm to 900 nm. Either fluorescence intensity or fluorescence lifetime (or both) may be measured. The composition may be contacted with analyte inside or outside of (i) an in vitro cultured cell or (ii) a cell or tissue in vivo.

It is yet another objective to provide use of the composition for manufacture of a diagnostic agent which detects analyte.

In processes for using and making these products, they which may then be subjected to further processing. It should be noted, however, that any claim directed to a product is not necessarily limited to such processes unless the particular steps of the process are recited in the product claim.

Further aspects of the invention will be apparent to a person skilled in the art from the following description of specific embodiments and generalizations thereto.

BRIEF DESCRIPTION OF THE DRAWINGS

FIG. 1 illustrates the supramolecular association of quencher and receptor, which prevents the electron transfer process and activates luminescence of the quantum dot.

FIG. 2 shows the absorption spectrum (a) of hydrophilic CdSe—ZnS core-shell quantum dots (1.5 µM, sodium phosphate buffer, pH=7.8, 20° C.). The emission spectra ($\lambda_{Ex}$=350 nm) of the same solution were recorded before (b) and after the consecutive addition of 1 (c, 4.1 µM) and 3 (d, 21 µM). Also shown is a Stern-Volmer plot (e) of hydrophilic CdSe—ZnS core-shell quantum dots (1.5 µM, sodium phosphate buffer, pH=7.8, 20° C., $\lambda_{Ex}$=350 nm) upon addition of increasing amounts of 1.

DESCRIPTION OF SPECIFIC EMBODIMENTS OF THE INVENTION

Figure 3:
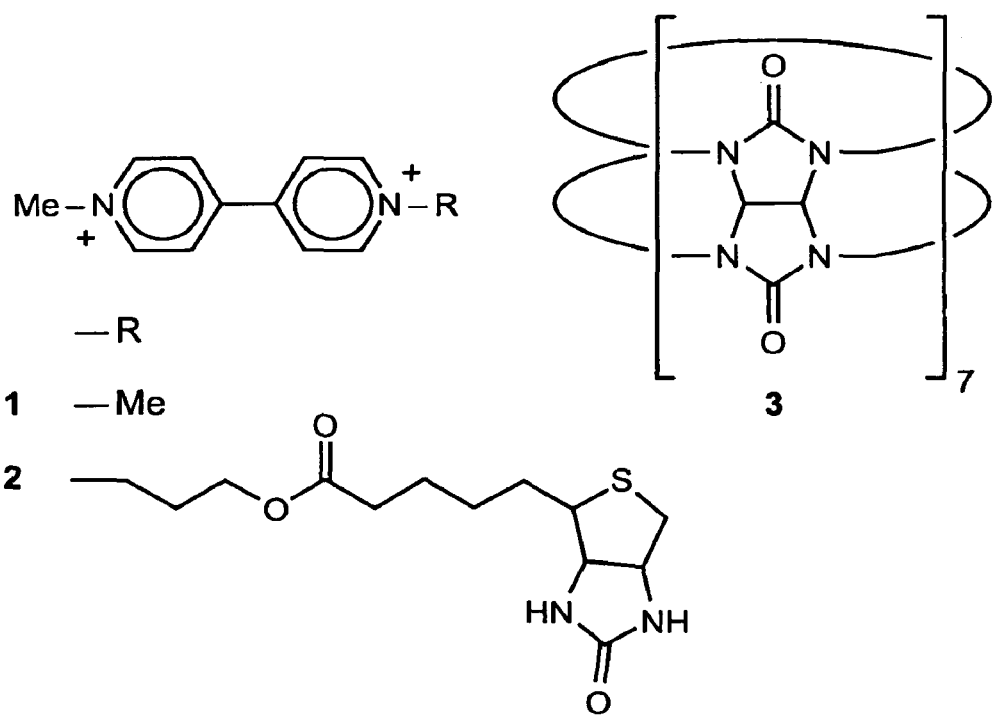
FIG. 3 illustrates bipyridinium-based quenchers 1 and 2 and a macro-cyclic receptor 3.

A composition is provided for use in a binding assay, which is comprised of at least one luminescent nanoparticle and one or more quencher molecules noncovalently associated (e.g., interactions that are electrostatic, hydrogen bonding, hydrophobic, or any combination thereof) on the surface of the nanoparticle, wherein the photoinduced transfer of electrons from an excited nanoparticle to adsorbed quencher molecule(s) (or vice versa) results in suppression (or enhancement) of luminescence. Electron transfer may occur from excited nanoparticle to quencher molecule, or from excited quencher molecule to nanoparticle. At least some quencher molecule(s) is stably (e.g., covalently or noncovalently) attached to ligand. The composition further comprises one or more receptors which specifically bind to ligand(s) stably attached to quencher molecule(s) (i.e., the molecule has a moiety which quenches luminescence and a ligand moiety which binds receptor). Receptor-ligand binding removes at least some, most, or almost all quencher molecule(s) from the nanoparticle's surface and restores its luminescence. Adsorbed quencher molecule(s) suppresses luminescence and will decreases the detectable signal from the nanoparticle; removal of quencher molecule(s) by receptor-ligand binding restores luminescence and increases the detectable signal from the nanoparticle. A change in luminescent signal may be detected by measuring intensity (e.g., the number of photons emitted at or around the emission wavelength of the nanoparticle) or lifetime (e.g., the time taken for 30% of the excited states of the nanoparticle to emit and return to ground state). The detectable change may be at least about ±10%, at least about ±20%, at least about ±30%, at least about ±40%, or at least about ±50%.

Nanoparticles are inorganic semiconductor nanocrystals with a mean diameter from about 1 nm to about 10 nm (preferably about 2 or 3 nm or more, preferably about 6 or 8 nm or less) that may or may not be coated. The nanocrystal (i.e., core) is "essentially spherical" as its shape resembles a spheroid (e.g., a porous or solid sphere) described by its diameter that varies by less than 5% or 10% as measured across any line through the center of an individual nanocrystal. In a composition, at least 60% of the nanocrystals may deviate less than 5% or 10% in root mean square (rms) diameter from each other. One or more coatings (i.e., shells, each of which are preferably of uniform thickness) may be another inorganic semiconductor and/or an organic layer (e.g., mixed hydrophobic/hydrophilic polymer) that optionally enhances quantum yield of its fluorescence and/or reduces oxidation of the nanocrystal. Exemplary semiconductors are CdS, CdSe, CdTe, ZnSe, ZnTe, and ternary and quaternary mixtures thereof. The other semiconductor coating preferably has a higher band gap energy: e.g., ZnS shell for a CdSe—ZnS core or ZnSe shell for a CdTe—ZnSe core. An exemplary organic layer is $SH(CH_2)_nX$, wherein n is from 8 to 15 and X is carboxylate or sulfonate, which aids solubility in aqueous solution. Thus, the nanoparticles preferably have a hydrophilic surface and are water soluble. The wavelength at maximum excitation of a nanoparticle (e.g., from about 300 nm to about 700 nm) may be theoretically calculated from known formulae. The wavelength at maximum emission of a nanoparticle may be in the visible or near infrared of the spectrum (e.g., from about 400 nm to about 900 nm).

A nanoparticle and quencher molecule(s) are noncovalently associated (e.g., by electrostatic or hydrophobic interaction, hydrogen bonding) with each other; association is reversible and preferably quencher molecule(s) are able to adsorb on/off the surface for multiple cycles. Nanoparticle and quencher molecule(s) are in close spatial proximity with each other such that electron transfer can occur between nanoparticle (acting as electron donor or acceptor) and quencher molecule(s) (acting as electron acceptor or donor, respectively). Receptor(s) is chosen to specifically recognize ligand(s) such as, for example, antigens, enzyme substrates or cofactors, cytokines or growth factors, fatty acids or lipids, glucose, neurotransmitters, or protein or steroid hormones. On individual nanoparticles, the quencher molecule(s) may be identical or different; the mean number of quencher molecules adsorbed on the individual nanoparticle may be at least three, at least five, at least seven, or at least nine.

One embodiment is based on the adsorption of cationic quencher molecule(s) on the surface of anionic luminescent nanoparticles. The adsorbed quencher moiety will efficiently suppress the emission character of the associated nanoparticles on the basis of photoinduced electron transfer. But in the presence of receptor(s) able to bind quencher-ligand molecule(s) and to prevent electron transfer to the quencher moiety, the luminescence of the nanoparticles is restored. A bipyridinium cation may be used as an electron acceptor. In another embodiment, anionic quencher molecule(s) is adsorbed on the surface of cationic luminescent nanoparticles. The adsorbed quencher moiety will efficiently enhance the emission character of the associated nanoparticles on the basis of photoinduced electron transfer. But in the presence of receptor(s) able to bind quencher-ligand molecule(s) and to prevent electron transfer from the quencher moiety, the luminescence of the nanoparticles is suppressed. A tertiary amine may be used as an electron donor. In other embodiments, the quencher molecule(s) may associate with the nanoparticle's surface by at least hydrophobic interaction and/or hydrogen bonding.

The diameter of the nanoparticle is chosen to emit a luminescent signal that is detectable. Characteristics of the nanoparticle and the quencher molecule are chosen to enable the efficient photoinduced transfer of electrons from the excited nanoparticle to the adsorbed quencher molecule(s). In particular, the quencher should be close to the nanoparticle's surface, and have a reduction potential as low as possible for an electron acceptor or an oxidation potential as low as possible for an electron donor. Similarly, characteristics of the quencher molecule and the receptor are chosen to enable the efficient removal of quencher molecule(s) adsorbed on the surface of the nanoparticle. The receptor may be a chelator, dye, nucleic acid, protein, or any other molecule that causes removal of quencher(s) adsorbed on the nanoparticle's surface. Complementary nucleic acids may be both receptor and ligand. Enzymes may be used to recognize metabolites such as glucose; receptors may be used to recognize hormones. Antibodies may be used to recognize antigens. Streptavidin may be used as a generalized receptor for ligands that have been biotinylated. The receptor may be soluble, bound to a solid substrate (e.g., cellulose, glass, polyacetate, polycarbonate, polystyrene, polyvinyl), or bound to a cell membrane (e.g., transmembrane or peripheral membrane).

The composition will usually be used as part of an in vitro binding assay (e.g., direct or competitive, homogenous or heterogeneous). But as an alternative, it may be added to cell culture medium, injected into biological fluid (e.g., blood, cerebrospinal fluid, interstitial fluid) or tissue through a catheter or with a syringe, or taken up by a cell or tissue which is then transplanted into the body. The composition in a pharmaceutically-acceptable carrier (e.g., sterile water for injection, saline solution, dextrose solution, etc. with or without buffering) may be administered (e.g., enteral or parenteral) to subjects (e.g., human or animal) as a diagnostic agent. To promote storage of kits or use in vivo, the composition is preferably aseptic (e.g., essentially free of bacterial, fungal, and viral contamination as determined by sterility testing) and nontoxic (e.g., less than 5 EU/kg as determined by pyrogen or endotoxin testing). A homogenous assay does not require separation of nanoparticles from the remainder of the composition prior to detection of luminescent signal but, if a heterogeneous assay requiring separation is desired, nanoparticles may be reversibly or nonreversibly attached to a solid substrate (e.g., optically-transparent bead, dipstick, microtiter plate, optically-transmitting fiber). The composition may further comprise blocking agent(s) and/or surfactant(s) to reduce nonspecific binding of receptor and ligand, but washing of the receptor-ligand complex is usually not required to improve specificity. The assay may detect analyte directly (i.e., analyte is the ligand) or indirectly (i.e., analyte is the receptor); it may be a competitor). The presence or the quantity of analyte may be detected. For example, the quencher and the ligand moieties may be connected directly (e.g., covalent bonding) or indirectly (e.g., bonded to either end of a hydrocarbon linker), the ligand or its competitor may be the analyte, and the receptor or its competitor may be the analyte.

Nanoparticles may be selectively activated by spatial- and/or temporal-specific excitation. Fluorescence emission may be visualized using a fluorescent microscope or another detector (e.g., camera) with the fluorescent signal recorded on a CCD diode array or photographic emulsion. Magnification and recording provide spatial and/or temporal resolution, respectively, of individual nanoparticles. Nanoparticles may also be examined for their optical characteristics by spectroscopy using a diode detector or photomultiplier tube. Nanoparticles may be excited by a light source (e.g., dye or gas laser, lamp, light emitting diode) focused on an illuminated portion of the microscope field or body. Luminescent signal may be separated for analysis with bandpass filters and/or dichroic glass. Moreover, events may be chronologically resolved by exciting the nanoparticle at a specific time for limited duration. The presence or quantity of analyte may be detected. A kit may comprise the composition and one or more standards of known quantity: amount (e.g., less than 1 pmol, from 1 pmol to 10 pmol, from 1 nmol to 10 nmol) or concentration (e.g., less than 1 µM, from 1 µM to 10 µM, from 1 mM to 10 mM).

We have designed a binding assay based on photoinduced transfer of electrons from a quantum dot to its organic acceptors/donors. Our method relies on noncovalent association of a quencher on the surface of a quantum dot (see FIG. 1). Photoinduced transfer of electrons from an excited quantum dot to the acceptor(s) will decrease the luminescent signal; alternatively, photo-induced transfer of electrons from an excited donor(s) to the quantum dot will increase the luminescent signal. The quantum dot's increased luminescence will result from adding a receptor able to sequester and remove acceptor(s) from the surface of the quantum dot, or decreased luminescence will result from adding a receptor able to sequester and remove donor(s) from the surface of the quantum dot. Thus, the presence of a receptor-quencher complex can be transduced into an increase or decrease in luminescent signal on the basis of this mechanism.

In order to demonstrate the viability of our design, we prepared CdSe—ZnS core-shell quantum dots coated with tri-n-octylphosphine oxide ligands in accordance with procedures reported in the literature.[33-34] Then, we exchanged the hydrophobic ligands with hydrophilic mercaptoacetate groups.[+,35] The resulting nanoparticles are soluble in water, absorb at 548 nm (a in FIG. 2), and emit at 563 nm (b). The addition of increasing amounts of methyl viologen (1 in FIG. 3), however, resulted in a significant decrease in luminescence intensity (c in FIG. 2) (the addition of either 1 or 2 to a solution of the quantum dots has no influence on the visible region of the absorption spectrum). Indeed, bipyridinium dications are known to accept electrons from excited CdSe and CdSe—ZnS core-shell quantum dots, quenching their luminescence.[36-37] The corresponding Stern-Volmer plot (e in FIG. 2) deviated from linearity at quencher concentrations greater than about 2.5 µM. This behavior indicates that the quenching mechanism is predominantly static below this particular concentration with a Stern-Volmer constant of about 0.45 µM$^{-1}$, while dynamic terms contribute significantly to quenching only at higher concentrations. These observations are consistent with the adsorbance of the dicationic quencher on the surface of the hydrophilic quantum dots as a result of electrostatic interactions with their anionic carboxylate groups.

Figure 4:
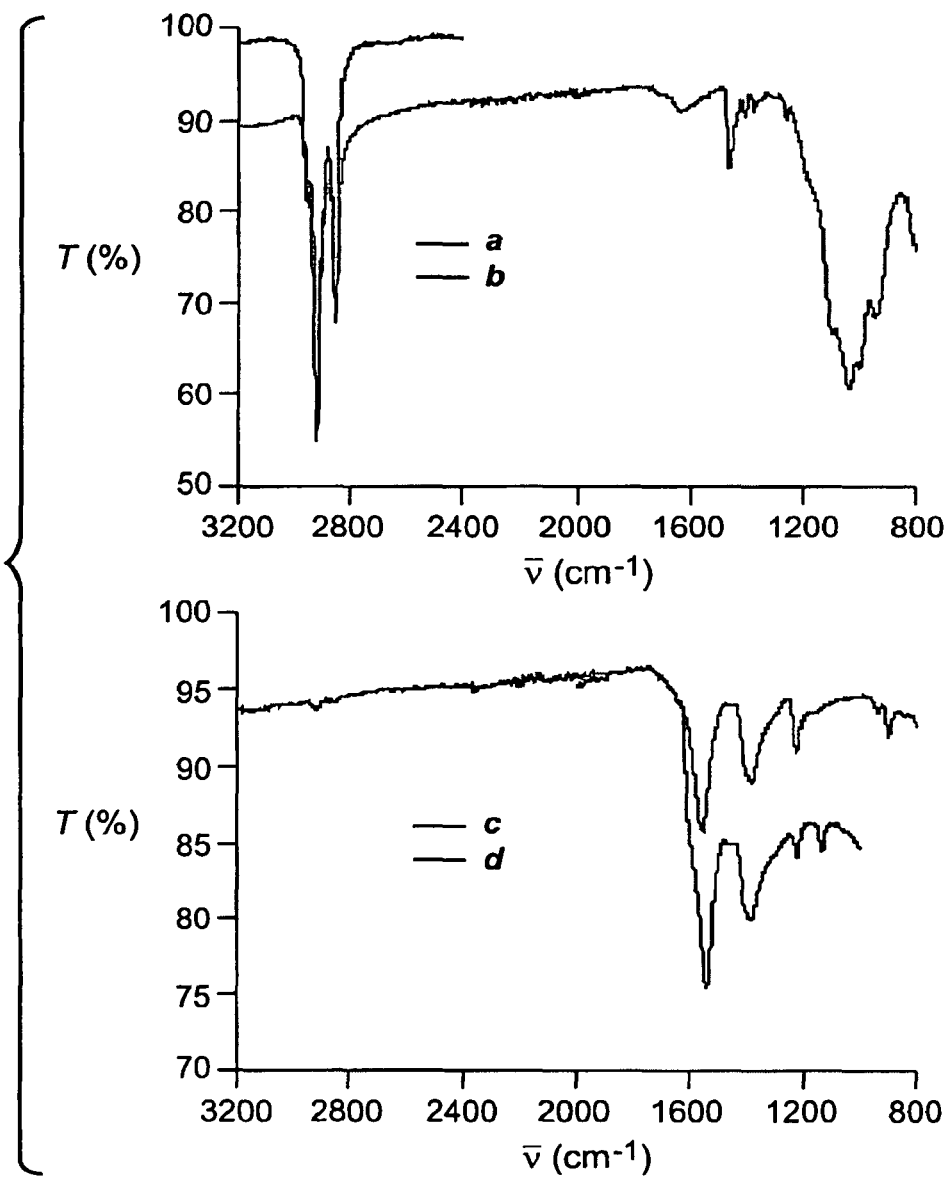
FIG. 4 shows the infrared spectra of neat tri-n-octylphopshine oxide (a), hydrophobic CdSe—ZnS core-shell quantum dots before (b) and after (c) treatment with mercaptoacidic acid and potassium hydroxide, and (d) potassium mercaptoacetate.
Figure 5:
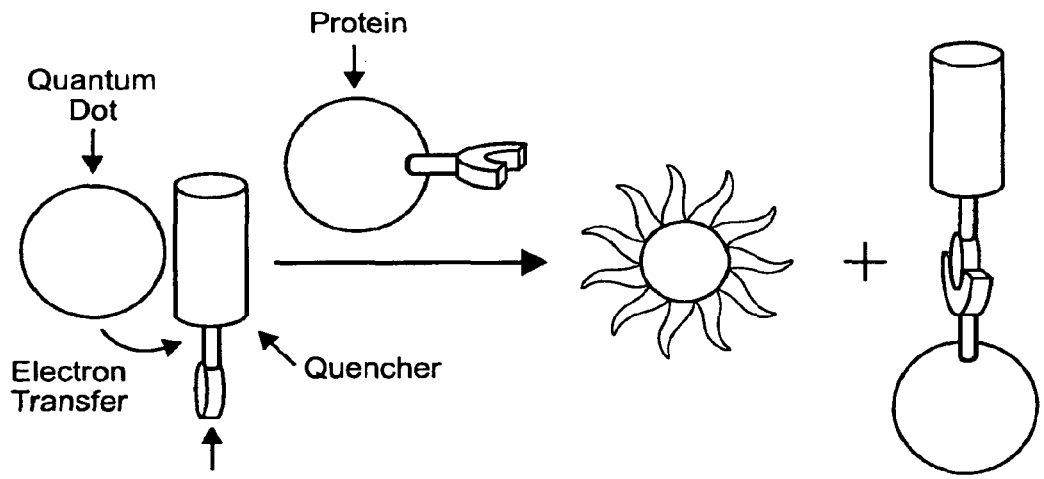
FIG. 5 illustrates the supramolecular association of protein and ligand, which prevents the electron transfer process and activates luminescence of the quantum dot.

The change imposed on the luminescence of the hydrophilic quantum dots by the quencher 1 can be reversed with the addition of an excess of cucurbituril (3 in FIG. 3). Indeed, this particular macrocyclic receptor is known to bind bipyridinium dications with high association constants in aqueous solutions.[36-39] Consistently, the emission spectrum (d in FIG. 2) recorded in the presence of an excess of 3 relative to 1 closely resembles the one recorded before the addition of 1 (b). The infrared spectra recorded before (b in FIG. 4) and after (c in FIG. 4) treatment of the CdSe—ZnS core-shell quantum dots with mercaptoacetic acid and potassium hydroxide show the disappearance of the [C—H] stretching vibrations at 2800 $cm^{-1}$ to 3000 $cm^{31\ 1}$ (a) for hydrophobic ligands and the appearance of the [C=O] stretching vibrations at 1300 $cm^{-1}$ to 1700 $cm^{-1}$ (d) for the hydrophilic ones. Thus, the receptor 3 binds the quencher, prevents the electron transfer process, and restores the ability of the hydrophilic quantum dots to emit light. In principle, the very same mechanism can be adapted to signal receptor-ligand interactions with changes in luminescence. For example, a ligand able to recognize a complementary receptor can be covalently attached to the quencher (see FIG. 5). In the absence of the receptor, the quencher can adsorb on the surface of a hydrophilic quantum dot and suppress its ability to emit light as a result of photoinduced electron transfer. But the supramolecular association of the ligand with the receptor can remove the quencher from the nanoparticle's surface and switch on its luminescence.

Figure 6:
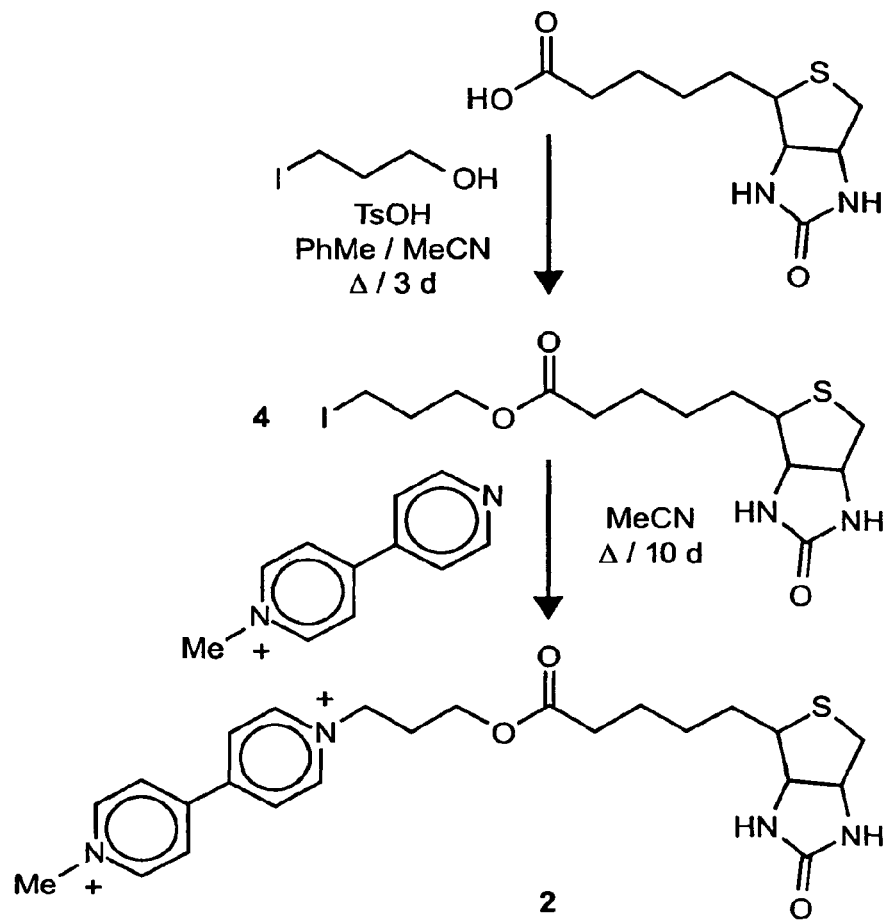
FIG. 6 is a schematic for the synthesis of a bipyridinium dication 2.

In order to test the potential of our operating principles to signal receptor-ligand interactions, we designed a compound (2 in FIG. 3) integrating a bipyridinium quencher and a biotin ligand within the same molecular skeleton and prepared this molecule in two synthetic steps (see FIG. 6). Once again, the luminescence of the hydrophilic quantum dots decreases upon exposure to 2 (a and b in FIG. 7) (the addition of either 1 or 2 to a solution of the quantum dots has no influence on the visible region of the absorption spectrum). As observed for 1, the corresponding Stern-Volmer plot (d in FIG. 7) is linear at relatively low quencher concentrations. It deviates from linearity only above about 2.5 µM, indicating that dynamic terms contribute significantly to quenching above this quencher concentration. The Stern-Volmer constant derived from the linear region of the plot, however, is only about 0.22 $\mu M^{-1}$. Presumably, the biotin tail of 2 disturbs the interaction between the appended quencher and the hydrophilic quantum dots, leading to a decrease in the Stern-Volmer constant of about 0.23 $\mu M^{-1}$ relative to 1.

Figure 7:
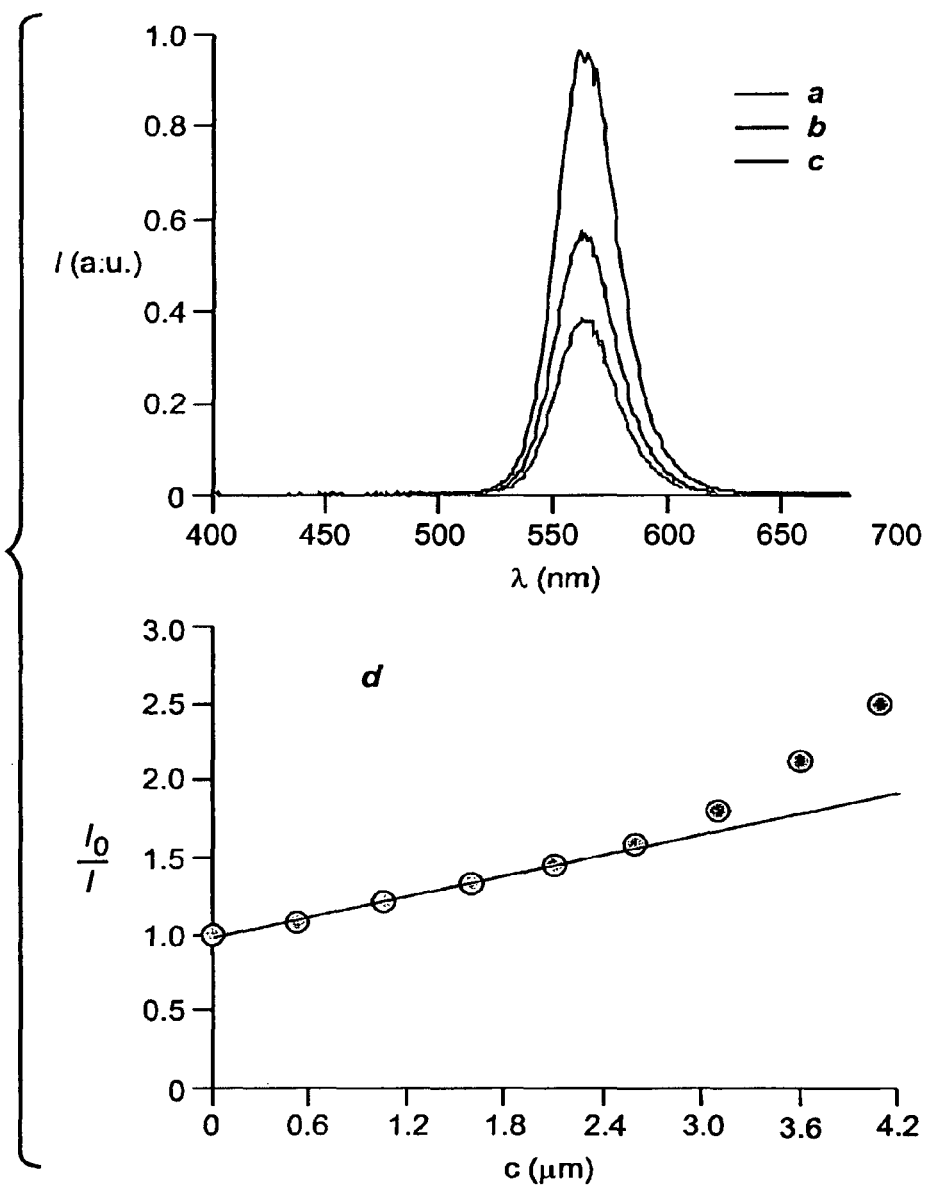
FIG. 7 shows the emission spectra of hydrophilic CdSe—ZnS core-shell quantum dots (1.5 µM, sodium phosphate buffer, pH=7.8, 20° C., $\lambda_{Ex}$=350 nm) recorded before (a) and after the consecutive addition of 2 (b, 4.1 µM) and streptavidin (c, 21 µM). Also shown is a Stern-Volmer plot (d) of hydrophilic CdSe—ZnS core-shell quantum dots (1.5 µM, sodium phosphate buffer, pH=7.8, 20° C., $\lambda_{Ex}$=350 nm) after addition of increasing amounts of 2.
Figure 8:
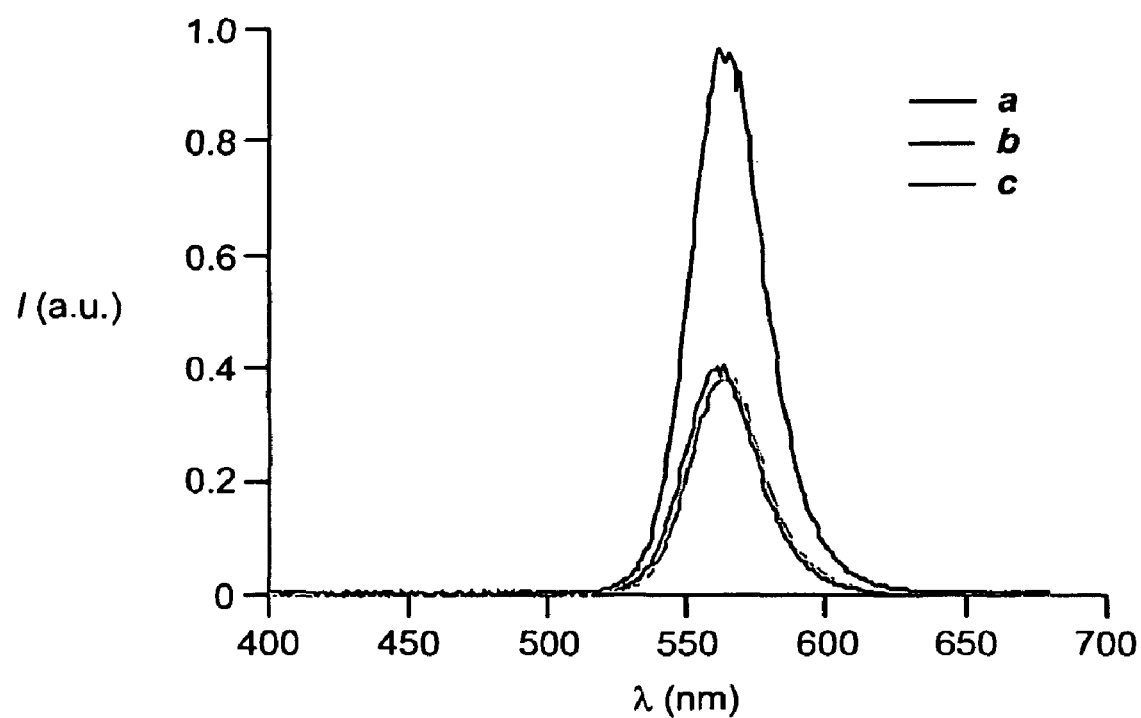
FIG. 8 shows the emission spectra of hydrophilic CdSe—ZnS core-shell quantum dots (1.5 µM, sodium phosphate buffer, pH=7.8, 20° C., $\lambda_{Ex}$=350 nm) recorded before (a) and after the consecutive addition of 2 (b, 4.1 µM) and bovine serum albumin (c, 7.4 µM).

The addition of increasing amounts of streptavidin to a mixture of the hydrophilic quantum dots and 2 leads to a luminescence enhancement (c in FIG. 7). The addition of 3, streptavidin or bovine serum albumin to a solution of the hydrophilic quantum dots has no influence on the emission spectrum in the absence of bipyridinium quenchers. Instead, the addition of bovine serum albumin has no influence of the emission spectrum under otherwise identical conditions (FIG. 8). Indeed, only streptavidin can bind the biotin ligand of 2 and, therefore, alter the quenching efficiency of the bipyridinium appendage.[40-41] Nonetheless, the original emission intensity is not fully restored even in the presence of a large excess of streptavidin. The luminescence increases only by 30% after the association of 2 and streptavidin, while it grows by 80% after the interaction of 1 and 3. The different behavior is presumably a result of the different binding modes of the two receptors. While streptavidin can only bind the biotin appendage of 2, the macrocycle 3 encapsulates the bipyridinium dication of 1 in its cavity, suppressing very effectively its quenching ability. Presumably, an adjustment in the length of the aliphatic spacer connecting the quencher to the ligand in 2 can be invoked to improve the luminescence enhancement upon streptavidin binding.

In summary, we have identified a mechanism to signal receptor-substrate interactions based on photoinduced electron transfer. Our method relies on the electrostatic adsorption of cationic quenchers on the surface of anionic quantum dots. The supramolecular association of the quenchers with target receptors prevents the electron transfer process and turns on the luminescence of the inorganic nanoparticles. In fact, this protocol can be adapted to probe protein-ligand interactions with luminescent measurements. Thus, our operating principles and choice of materials can eventually lead to the development of valuable binding assays for biorelevant targets relying on the unique photophysical properties of semiconductor quantum dots.

Methods. Chemicals were purchased from commercial sources with the exception of 1-methyl-4,4'-pyridylpyridinium iodide, which was synthesized in accordance with Feng, D.-J., Li, X.-Q., Wang, X.-Z., Jiang, X.-K., & Li, Z.-T. (2004) *Tetrahedron* 60, 6137-6144. Infrared absorption spectra were recorded with a Perkin-Elmer Spectrum One Fourier transform spectrometer. Visible absorption spectra were recorded with a Varian Cary 100 Bio spectrometer, using quartz cells with a path length of 0.5 cm. Emission spectra were recorded with a Varian Cary Eclipse spectrometer in aerated solutions. Fast atom bombardment mass spectra (FABMS) were recorded with a VG Mass Lab Trio-2 in a 3-nitrobenzyl alcohol matrix. Nuclear magnetic resonance (NMR) spectra were recorded with Bruker Avance 400 and 500 spectrometers.

Hydrophobic CdSe—ZnS Core-Shell Quantum Dots. A mixture of CdO (51 mg, 0.4 mmol), tetra-n-decylphosphonic acid (223 mg, 0.8 mmol), tri-n-octylphosphine oxide (3.78 g, 9.8 mmol) was heated at 320° C. under Ar until a clear solution was obtained. Then, the temperature was lowered to 220° C. and a solution of Se (41 mg, 0.5 mmol) in tri-n-octylphosphine (2.4 mL) was added. After the addition, the mixture was maintained at 200° C. for 40 min. Then, the temperature was lowered to 120° C. and a solution of $ZnEt_2$ (1.6 mL, 0.16 mmol) and hexamethyldisilathiane (0.30 mL, 1.4 mmol) in tri-n-octylphosphine (5 mL) was added dropwise. After the addition, the mixture was maintained at 70° C. for 5 h. After cooling down to ambient temperature, MeOH (200 mL) was added and the resulting precipitate was filtered and dissolved in CHCl3 (50 mL). This procedure was repeated three more times and then the solvent was distilled off under reduced pressure to afford the CdSe—ZnS core-shell quantum dots (367 mg) as a reddish powder.

Hydrophilic CdSe—ZnS Core-Shell Quantum Dots. A solution of CdSe—ZnS core-shell quantum dots (25 mg) and mercaptoacetic acid (2 mL) in $CHCl_3$ (30 mL) was heated under reflux for 3 h. After cooling down to ambient temperature, the mixture was subjected to centrifugation. The residue was suspended in $CHCl_3$ (15 mL) and subjected to centrifugation. This treatment was repeated four additional times. The resulting solid was suspended in MeOH (15 mL) and subjected to centrifugation. This treatment was repeated two additional times. The residue was dried under reduced pressure and suspended in $H_2O$ (5 mL). Aqueous KOH (0.1 M) was added dropwise until a clear solution was obtained. After the addition of $Me_2CO$ (10 mL), the mixture was subjected to centrifugation to afford the modified CdSe—ZnS core-shell quantum dots (20 mg) as a reddish powder.

5-(2-Oxohexahydrothieno[3,4-d]imidazol-6-yl)-pentanoic Acid 3-Iodopropyl Ester (4). A solution of biotin (125 mg, 0.5 mmol), 3-iodo-1-propanol (150 μL, 1.6 mmol) and TsOH (10 mg, 0.05 mmol) in PhMe (50 mL)) was heated under reflux and Ar for 3 d in a Dean-Stark apparatus. After cooling down to ambient temperature, the mixture was filtered and the solvent distilled off under reduced pressure. The residue was dissolved in $CH_2Cl_2$ (30 mL) and washed with $H_2O$ (5 mL). The organic phase was dried ($MgSO_4$) and concentrated under reduced pressure to yield 4 (75 mg, 36%) as a white solid. FABMS: m/z=413 $[M+H]^+$; $^1H$-NMR (400 MHz, $CDCl_3$): δ=1.40-1.45 (2H, m), 1.61-1.75 (4H, m), 2.10-2.16 (2H, m), 2.30 (2H, t, 7 Hz), 2.79 (1H, d, 13 Hz), 2.88 (1H, dd, 5 and 13 Hz), 3.15-3.18 (1H, m), 3.22 (2H, t, 7 Hz), 4.13 (2H, t, 6 Hz), 4.42-4.45 (1H, m), 4.61-4.65 (1H, m), 7.22 (1H, d, 8 Hz); 7.72 (1H, d, 8 Hz); $^{13}C$-NMR (100 MHz, $CDCl_3$): δ=25.0, 28.4, 28.8, 32.6, 34.2, 40.5, 55.8, 61.8, 63.6, 64.4, 164.5, 173.9.

1-Methyl-1'-(3-(5-(2-Oxohexahydrothieno[3,4-d]imidazol-6-yl)-pentanoxy)-propyl)-4,4'-Bipyridinium Bisiodide (2). A solution of 4 (37 mg, 0.09 mmol) and 1-methyl-4,4'-pyridylpyridynium iodide (9 mg, 0.03 mmol) in MeCN (15 mL) was heated under reflux and Ar for 10 d. After cooling down to ambient temperature, the solvent was distilled off and the residue was washed with MeCN (4 mL) to yield 2 (6 mg, 28%) as an orange solid. FABMS: m/z=457 $[M-2I]^+$; $^1H$-NMR (500 MHz, $CD_3OD$): δ=1.45-1.49 (2H, m), 1.53-1.71 (4H, m), 2.29-2.31 (2H, m), 2.49-2.51 (2H, m), 2.73 (1H, dd, 4 and 12 Hz), 2.93 (1H, dd, 5 and 12 Hz), 3.20-3.23 (1H, m), 4.28-4.32 (3H, m), 4.48-4.52 (2H, m), 4.54 (3H, s), 4.77 (2H, d, 8 Hz), 8.69 (2H, d, 6 Hz), 8.73 (2H, d, 6 Hz), 9.21 (2H, d, 6 Hz), 9.34 (2H, d, 7 Hz).

REFERENCES

1. Bawendi, M. G., Steigerwald, M. L., & Brus, L. E. (1990) Ann. Rev. Phys. Chem. 41, 477-496.
2. Alivisatos, A. P. (1996) Science 271, 933-937.
3. Efros, Al. L., & Rosen, M. (2000) Ann. Rev. Mater. Sci. 30, 475-521.
4. Yoffe, A. D. (2001) Adv. Phys. 50, 1-208.
5. Burda, C., Chen, X. B., Narayana, R., & El-Sayed, M. A. (2005) Chem. Rev. 105, 1025-1102.
6. Niemeyer, C. M. (2003) Angew. Chem. Int. Ed. 42, 5796-5800.
7. Willner, I., & Katz, E. (2004) Angew. Chem. Int. Ed. 43, 6042-6108.
8. Alivisatos, A. P. (2004) Nature Biotechnol. 22, 47-52.
9. Rosi, N. L., & Mirkin, C. A. (2005) Chem. Rev. 105, 1547-1562.
10. Gao, X., Yang, L., Petros, J. A., Marshall, F. F., Simons, J. W., & Nie, S. (2005) Curr. Op. Biotechnol. 16, 63-72.
11. Medintz, I. G., Uyeda, H. T., Goldam, E. R., & Mattoussi, H. (2005) Nature Mater. 4, 435-446.
12. Michalet, X., Pinaud, F. F., Bentolila, L. A., Tsay, J. M., Doose, S., Li, J. J., Sundaresan, G., Wu, A. M., Gambhir, S. S., & Weiss, S. (2005) Science 307, 538-544.
13. Ricco, A. J., & Crooks, R. M., Eds. (1998) Acc. Chem. Res. 31, 199-324.
14. Ellis, A. B., & Walt, D. R., Eds. (2000) Chem. Rev. 100, 2477-2738.
15. Fabbrizzi, L., Ed. (2000) Coord. Chem. Rev. 205, 1-232.
16. de Silva, A. P., & Tecilla, P., Eds. (2005) J. Mater. Chem. 15, 2617-2976.
17. Clapp, A. R., Medintz, I. L., & Mattoussi, H. (2006) Chem Phys Chem 7, 47-57.
18. Willard, D. M., Carillo, L. L., Jung, J., & Van Orden, A. (2001) Nano Lett. 1, 469-474.
19. Wang, S., Mamedova, N., Kotov, N. A., Chen, W., & Studer, J. (2002) Nano Lett. 2, 817-822.
20. (a) Tran, P. T., Goldman, E. R., Anderson, G. P., Mauro, J. M., & Mattoussi, H. (2002) Phys. Stat. Sol. 229, 427-432. (b) Medintz, I. L., Clapp, A. R., Mattoussi, H., Goldman, E. R., Fisher, B., & Mauro, J. M. (2003) Nature Mater. 2, 630-638. (c) Medintz, I. L., Clapp, A. R., Melinger, J. S., Deschamps, J. R., & Mattoussi, H. (2005) Adv. Mater. 17, 2450-2455. (d) Goldman, E. R., Medintz, I. L., Whitley, J. L., Hayhurst, A., Clapp, A. R., Uyeda, H. T., Deschamps, J. R., Lassman, M. E., & Mattoussi, H. (2005) J. Am. Chem. Soc. 127, 6744-6751.
21. (a) Patolsky, F., Gill, R., Weizmann, Y., Mokari, T., Banin, U., & Willner, I. (2003) J. Am. Chem. Soc. 125, 13918-13919. (b) Gill, R., Willner, I., Shweky, I., & Banin, U. (2005) J. Phys. Chem. B 109, 23715-23719.
22. Nagasaki, N., Ishii, T., Sunaga, Y., Watanabe, Y., Otsuka, H., & Kataoka, K. (2004) Langmuir 20, 6396-6400.
23. Hildebrandt, N., Charbonnière, L. J., Beck, M., Ziessel, R. F., & Löhmannsröben, H.-G. (2005) Angew. Chem. Int'l Ed. 44, 1-5.
24. Geissbuehler, I., Hovius, R., Martinez, K. L., Adrian, M., Thampi, K. R., & Vögel, H. (2005) Angew. Chem. Int'l Ed. 44, 1388-1392.
25. Dyadyusha, L., Yin, H., Jaiswal, S., Brown, T., Baumberg, J. J., Booy, F. P., & Melvin, T. (2005) Chem. Commun., 3201-3203.
26. Hohng, S., & Ha, T. (2005) Chem Phys Chem 6, 956-960.
27. Oh, E., Hong, M.-Y., Lee, D., Nam, S.-H., Yoon, H. C., & Kim, H.-S. (2005) J. Am. Chem. Soc. 127, 3270-3271.
28. Bakalova, R., Zhelev, Z., Ohba, H., & Baba, Y. (2005) J. Am. Chem. Soc. 127, 11328-11335.
29. Zhang, C.-Y., Yeh, H.-C., Kuroki, M. T., & Wang, T.-H. (2005) Nature Mater. 4, 826-831.
30. Chen, C.-Y., Cheng, C.-T., Lai, C.-W., Wu, P.-W., Wu, K.-C., Chou, P.-T., Chou, Y.-H., & Chiu, H.-T. (2006) Chem. Commun., 263-265.
31. Sandros, M. G., Gao, D., & Benson, D. E. (2005) J. Am. Chem. Soc. 127, 12198-12199.
32. Palaniappan, K., Xue, C., Arumugam, G., Hackney, S. A., & Liu, J. (2006) Chem. Mater. 18, 1275-1280.
33. Dabbousi, B. O., Rodriguez-Viejo, J., Mikulec, F. V., Heine, J. R., Mattoussi, H., Ober, R., Jensen, K. F., & Bawendi, M. G. (1997) J. Phys. Chem. B 101, 9463-9475.
34. Peng, Z. A., & Peng, X. (2001) J. Am. Chem. Soc. 123, 183-184.
35. Chan, W. C. W., & Nie, S. (1998) Science. 281, 2016-2018.
36. Burda, C., Green, T. C., Link, S., & El-Sayed, M. A. (1999) J. Phys. Chem. B 103, 1783-1788
37. Yildiz, I., & Raymo, F. M. (2006) J. Mater. Chem. 16, 1118-1120.
38. (a) Ong, W., Gómez-Kaifer, M., & Kaifer, A. E. (2002) Org. Lett. 4, 1791-1794. (b) Ong, W., & Kaifer, A. E. (2004) J. Org. Chem. 69, 1383-1385.
39. Kim, H.-J., Keon, W. S., Ko, Y. H., & Kim, K. (2002) Proc. Natl. Acad. Sci. USA 99, 5007-5011.
40. Hendrickson, W. A., Pahler, A., Smith, J. L., Satow, Y., Merritt, E. A., & Phizackerley, R. P. (1989) Proc. Natl. Acad. Sci. USA 86, 2190-2194.
41. Weber, P. C., Ohlendorf, D. H., Wendoloski, J. J., & Salemme, F. R. (1989) Science 243, 85-88.

Patents, patent applications, books, and other publications cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method for detection of at least presence or quantity of an analyte, said method comprising:
   (a) contacting (i) at least one luminescent nanoparticle having a surface and comprising an essentially spherical, semiconductor nanocrystal, (ii) one or more quencher-ligand molecules which may be noncovalently associated on said surface, thereby modulating a luminescent signal of said nanoparticle, or may be removed from said surface, thereby modulating a luminescent signal of said nanoparticle, wherein said molecule(s) are comprised of quencher and ligand moieties, (iii) one or more receptors which may bind at least one quencher-ligand molecule, and (iv) a solution which might contain an analyte, wherein binding of receptor and ligand removes quencher molecule(s) from said luminescent nanoparticle's surface;
   (b) measuring whether or not there is a detectable change in luminescent signal; and
   (c) correlating the change in luminescent signal with detection of at least presence or quantity of the analyte.

2. The method according to claim 1, wherein fluorescence absorption of the nanoparticle is excited at one or more wavelengths from 300 nm to 700 nm.

3. The method according to claim 1, wherein fluorescent emission of the nanoparticle is measured at one or more wavelengths from 400 nm to 900 nm.

4. The method according to claim 1, wherein fluorescence intensity is measured.

5. The method according to claim 1, wherein fluorescence lifetime is measured.

6. The method according to claim 1, wherein the analyte is contacted inside or outside of a cultured cell in vitro.

7. The method according to claim 1, wherein the analyte is contacted inside or outside of a cell or tissue in vivo.

8. The method according to claim 1, wherein at least one nanoparticle has a mean diameter from 1 nm to 10 nm.

9. The method according to claim 1, wherein at least one nanocrystal comprises CdSe or CdTe.

10. The method according to claim 1, wherein at least one nanoparticle is coated.

11. The method according to claim 10, wherein at least one nanoparticle is coated with an inorganic semiconductor layer and/or an organic layer.

12. The method according to claim 11, wherein at least one nanoparticle is coated with an inorganic semiconductor layer comprising ZnS or ZnSe.

13. The method according to claim 11, wherein at least one nanoparticle is coated with a hydrophilic organic layer.

14. The method according to claim 1, wherein at least one quencher is a bipyridinium cation.

15. The method according to claim 1, wherein at least one quencher is a tertiary amine.

16. The method according to claim 1, wherein at least one receptor is a nucleic acid.

17. The method according to claim 1, wherein at least one receptor is a protein.

18. The method according to claim 1, wherein said analyte is ligand or its competitor.

19. The method according to claim 1, wherein said analyte is receptor or its competitor.

* * * * *